US00PP25280P2

(12) United States Plant Patent
van den Top

(10) Patent No.: US PP25,280 P2
(45) Date of Patent: Feb. 3, 2015

(54) *HOSTA* PLANT NAMED 'SLEEPING STAR'

(50) Latin Name: ***Hosta* hybrid**
Varietal Denomination: Sleeping Star

(71) Applicant: Hendrik Jan van den Top, Barneveld (NL)

(72) Inventor: Hendrik Jan van den Top, Barneveld (NL)

( * ) Notice: Subject to any disclaimer, the term of this patent is extended or adjusted under 35 U.S.C. 154(b) by 114 days.

(21) Appl. No.: 13/815,272

(22) Filed: Feb. 15, 2013

(51) Int. Cl.
*A01H 5/00* (2006.01)

(52) U.S. Cl.
USPC ..... Plt./353

(58) Field of Classification Search
USPC ..... Plt./353
See application file for complete search history.

*Primary Examiner* — Susan McCormick Ewoldt
(74) *Attorney, Agent, or Firm* — C. A. Whealy

(57) ABSTRACT

A new and distinct cultivar of *Hosta* plant named 'Sleeping Star', characterized by its upright to outwardly spreading foliage and mostly upright flower scapes; dark green and creamy white variegated leaves; white to light greyed purple-colored flowers that are positioned above the foliar plane on strong scapes; and good garden performance.

2 Drawing Sheets

Botanical designation: *Hosta* hybrid.
Cultivar denomination: 'SLEEPING STAR'.

BACKGROUND OF THE INVENTION

The present invention relates to a new and distinct cultivar of *Hosta* plant, botanically known as *Hosta* hybrid and hereinafter referred to by the name 'Sleeping Star'.

The new *Hosta* plant is a naturally-occurring whole plant mutation of the *Hosta* hybrid 'Sleeping Beauty', not patented. The new *Hosta* plant was discovered and selected by the Inventor in a controlled outdoor nursery environment in Barneveld, The Netherlands during the summer of 2005.

Asexual reproduction of the new *Hosta* plant by divisions in a controlled outdoor nursery environment in Barneveld, The Netherlands since the spring of 2007 has shown that the unique features of this new *Hosta* plant are stable and reproduced true to type in successive generations.

SUMMARY OF THE INVENTION

Plants of the new *Hosta* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sleeping Star'. These characteristics in combination distinguish 'Sleeping Star' as a new and distinct *Hosta* plant:

1. Upright to outwardly spreading foliage with mostly upright flower scapes.
2. Dark green and creamy white variegated leaves.
3. White to light greyed purple-colored flowers that are positioned above the foliar plane on strong scapes.
4. Good garden performance.

Plants of the new *Hosta* differ primarily from plants of the parent, 'Sleeping Beauty', primarily in leaf color as plants of 'Sleeping Beauty' have leaves with much narrower white-colored edges.

Plants of the new *Hosta* can be compared to plants of 'Great Escape', disclosed in U.S. Plant Pat. No. 19,003. Plants of the new *Hosta* and 'Great Escape' differ primarily in leaf color as plants of 'Great Escape' have green and white variegated leaves.

BRIEF DESCRIPTION OF THE PHOTOGRAPHS

The accompanying colored photographs illustrate the overall appearance of the new *Hosta* plant showing the colors as true as it is reasonably possible to obtain in colored reproductions of this type. Colors in the photographs may differ slightly from the color values cited in the detailed botanical description which accurately describe the colors of the new *Hosta* plant.

The photograph on the first sheet comprises a top perspective view of a typical flowering plant of 'Sleeping Star' grown in a container.

The photograph on the second sheet is a close-up view of a typical inflorescence of 'Sleeping Star'.

DETAILED BOTANICAL DESCRIPTION

The aforementioned photographs and following observations, measurements and values describe plants grown during the summer in 17-cm containers in an outdoor nursery in Barneveld, The Netherlands and under cultural practices typical of commercial production. During the production of the plants, day temperatures ranged from 16° C. to 28° C. and night temperatures ranged from 8° C. to 18° C. Plants were 16 months old when the photographs and description were taken. In the following description, color references are made to The Royal Horticultural Society Colour Chart, 2007 Edition, except where general terms of ordinary dictionary significance are used.

Botanical classification: *Hosta* hybrid 'Sleeping Star'.

Parentage: Naturally-occurring whole plant mutation of the *Hosta* hybrid 'Sleeping Beauty', not patented.

Propagation:

*Type*.—By divisions.

*Root description*.—Medium in thickness, fibrous; creamy white in color.

*Rooting habit*.—Moderate branching; medium density.

Plant description:

*Plant form and growth habit*.—Herbaceous flowering perennial plant; mounded plant form with upright to outwardly spreading foliage and upright flower scapes; flowering stems and leaves basal; low vigor; white to light greyed purple-colored flowers that are positioned above the foliar plane on strong scapes.

*Plant height* (*soil level to top of foliar plane*).—About 13.9 cm.

*Plant height* (*soil level to top of inflorescences*).—About 20.7 cm.

*Plant width* (*spread*).—About 25.9 cm.

Foliage description:

*Arrangement and appearance*.—Leaves arranged in a basal rosette; leaves simple and generally symmetrical.

*Leaf length*.—About 9.1 cm.

*Leaf width*.—About 4.8 cm.

*Shape*.—Narrowly ovate.

*Apex*.—Long apiculate.

*Base*.—Short attenuate to obtuse.

*Margin*.—Entire; undulate.

*Texture, upper and lower surfaces*.—Smooth, glabrous; moderately rugose.

*Venation pattern*.—Camptodrome.

*Color*.—Developing leaves, upper surface: Center, close to 137A, 147A and 147B; towards the margins, close to 151C to 151D. Developing leaves, lower surface: Center, close to 189A and 191A; towards the margins, close to 150C. Fully expanded leaves, upper surface: Center, close to N189A; towards the margins, close to between 155D and 158D; venation, similar to lamina colors, that is, close to N189A and between 155D and 158D. Fully expanded leaves, lower surface: Center, close to 189A; towards the margins, close to between 155D and 158D; venation, similar to lamina colors, that is, close to 189A and between 155D and 158D.

*Petioles*.—Length: About 9.2 cm. Width: About 4 mm. Height: About 4.5 mm. Texture, upper and lower surfaces: Smooth, glabrous. Color, upper surface: Center, close to 189A; towards the margins, close to 155A. Color, lower surface: Center, close to 143B and 144A; towards the margins, close to 155A.

Flower description:

*Flower type and flowering habit*.—Single campanulate flowers with fused perianth arranged on terminal racemes; flowers face mostly outwardly to slightly drooping; panicles narrowly conical in shape; freely flowering habit with about 19 flowers per raceme.

*Fragrance*.—None detected.

*Natural flowering season*.—Flowering continuous from June into August in The Netherlands.

*Postproduction longevity*.—Flowers last about five days the plant; flowers not persistent.

*Flower buds*.—Height: About 2.4 cm. Diameter: About 8 mm. Shape: Oblanceolate. Color: Close to NN155D; towards the apex, close to between N155A and N187D.

*Inflorescence height*.—About 22.8 cm.

*Inflorescence diameter*.—About 6.2 cm.

*Flower diameter*.—About 1.4 cm.

*Flower depth*.—About 4 cm.

*Perianth*.—Arrangement: Three interior tepals arranged in a single whorl surrounded by an outer whorl of three exterior tepals; lower 65% of tepals fused; upper 35% of tepals flaring into a trumpet shape. Tepal length: About 3.6 cm. Tepal width: About 6 mm. Tepal lobe shape: Oblanceolate. Tepal apex: Acute. Tepal margin: Entire. Tepal texture, upper and lower surfaces: Smooth, glabrous. Tepal color: Developing and fully expanded tepals, upper surface: Close to between N155A and N187D; color becoming closer to between N155A and 84D with development. Developing and fully expanded tepals, lower surface: Close to between N155A and N187D.

*Flower bracts*.—Quantity per flower: One, positioned at the base of the pedicel. Length: About 1.8 cm. Width: About 1 cm. Shape: Narrowly ovate; concave. Apex: Acute. Base: Cuneate. Margin: Entire. Texture, upper and lower surfaces: Smooth, glabrous. Color, upper and lower surfaces: Close to 138A; towards the margins, close to N187D.

*Peduncles* (*scapes*).—Length: About 21.1 cm. Diameter: About 3 mm. Aspect: About 15° from vertical. Strength: Strong. Texture: Smooth, glabrous. Color: Close to 189B.

*Pedicels*.—Length: About 5 mm. Diameter: About 1.5 mm. Aspect: About 45° from peduncle axis. Strength: Strong. Texture: Smooth, glabrous. Color: Close to 144B.

*Reproductive organs*.—Stamens: Quantity per flower: Typically six. Filament length: About 2.8 cm. Filament color: Close to 150D. Anther shape: Narrowly oblong; dorsifixed. Anther length: About 3 mm. Anther color: Close to N170B. Pollen amount: Scarce to moderate. Pollen color: Close to 15A. Pistils: Quantity per flower: One. Pistil length: About 3.3 cm. Style length: About 3 cm. Style color: Close to 150D. Stigma shape: Crested. Stigma color: Close to NN155C. Ovary color: Close to 150C.

*Seeds and fruits*.—Seed and fruit development have not been observed on plants of the new *Hosta*.

Disease & pest resistance: Plants of the new *Hosta* have not been noted to be resistant to pathogens and pests common to *Hosta* plants.

Garden performance: Plants of the new *Hosta* have been observed to have good garden performance and to tolerate rain, wind and high temperatures about 32° C., and to be hardy to USDA Hardiness Zone 5.

It is claimed:

1. A new and distinct *Hosta* plant named 'Sleeping Star' as illustrated and described.

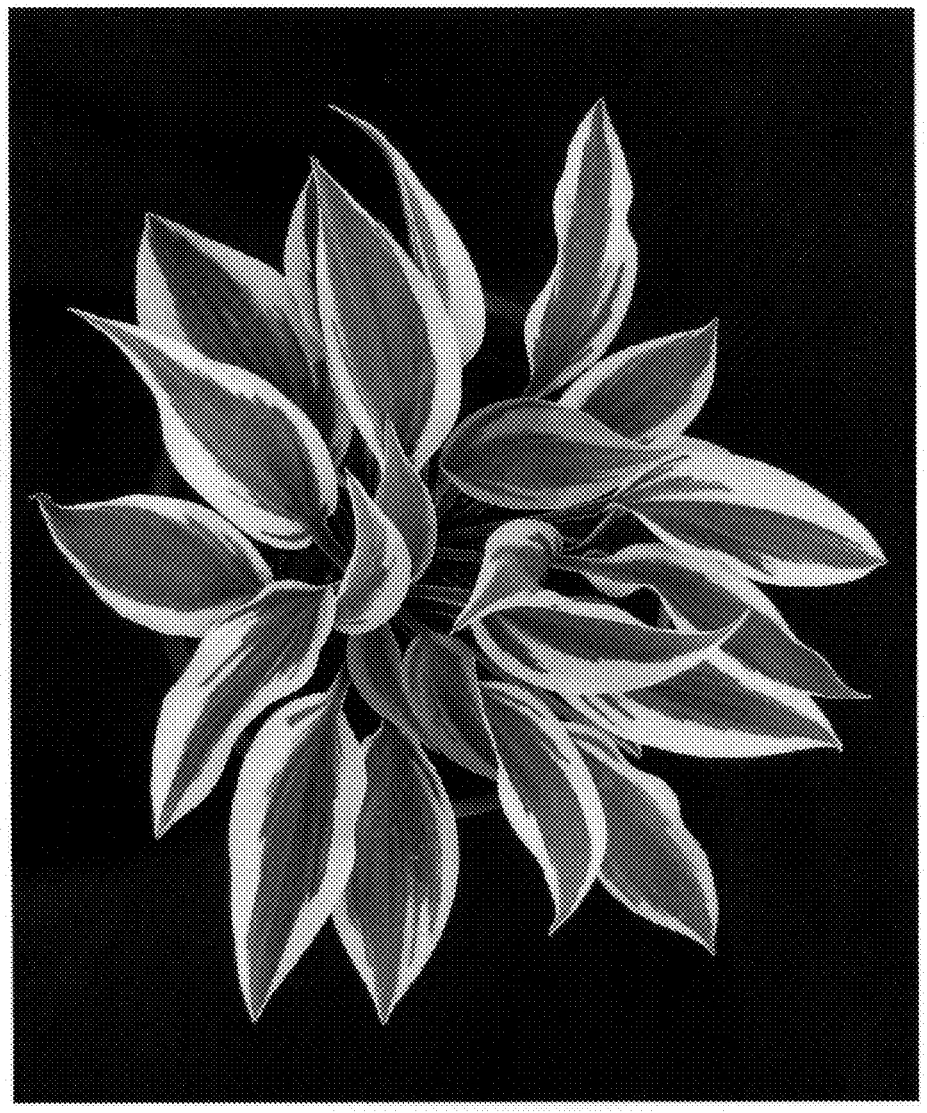

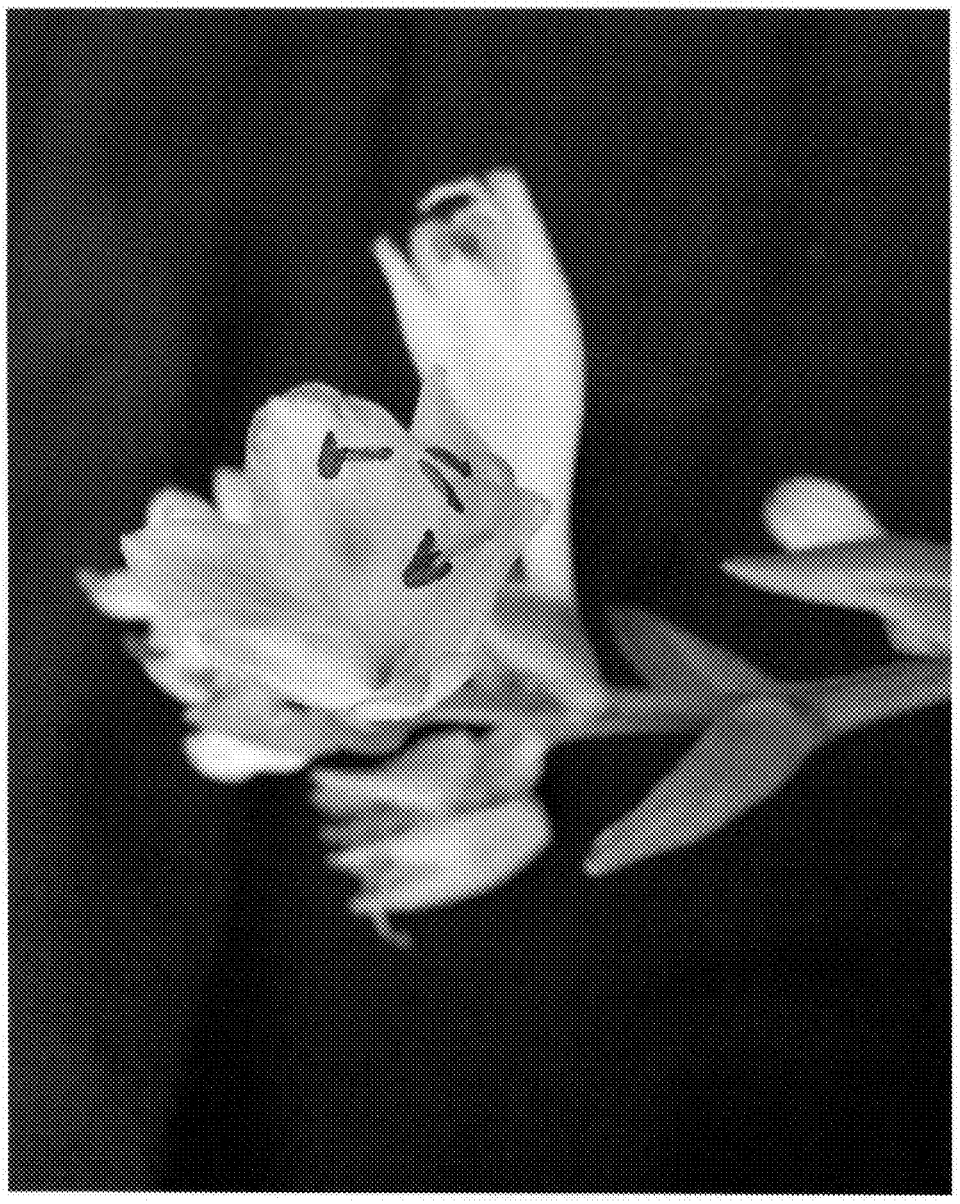

* * * * *